(12) United States Patent
Kuzma et al.

(10) Patent No.: US 6,275,736 B1
(45) Date of Patent: Aug. 14, 2001

(54) HAIR CLIP RETENTION SYSTEM FOR HEADPIECE OF COCHLEAR IMPLANT SYSTEM

(75) Inventors: Janusz A. Kuzma; Lani A. Smith, both of Englewood, CO (US); Richard P. Malmgren, Castaic, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/312,158

(22) Filed: May 14, 1999

Related U.S. Application Data

(60) Provisional application No. 60/097,965, filed on Aug. 26, 1998, and provisional application No. 60/087,654, filed on Jun. 2, 1998.

(51) Int. Cl.[7] .................................................. A61N 1/36
(52) U.S. Cl. ............................................. 607/57; 128/903
(58) Field of Search ....................... 607/55–57; 128/903

(56) References Cited

U.S. PATENT DOCUMENTS 5,776,172   7/1998   Schulman et al. ..................... 607/56

*Primary Examiner*—Jeffrey R. Jastrzab
(74) *Attorney, Agent, or Firm*—Bryant R. Gold

(57) ABSTRACT

A hair clip for use with a cochlear implant system retains a headpiece assembly, including a transmitting coil, in an aligned position relative to an implanted stimulator. In one embodiment, the hair clip provides a retention system that uses a magnet which forms part of the transmitting coil. A comb or plurality of prongs forms part of the retention system. In another embodiment, the comb has central teeth that are made from ferromagnetic material, and typically also has a non-central teeth that are made from non-ferromagnetic material. The comb is placed and secured in the patient's hair over the area where a cochlear implant is implanted. The transmitting coil is then placed next to the comb, and the magnet within the transmitting coil attaches to the ferromagnetic teeth of the comb. In another embodiment, the transmitting coil is housed in a headpiece, and the headpiece and comb or hair clip are fastened together, along an edge of the comb or hair clip where the teeth or prongs are bonded, with a hinge attachment spring. In a further embodiment, the hair clip is formed from a single sheet of stainless steel, and a plurality of prongs engage a lower surface of the headpiece while a retaining band, with an integral spring, securely holds the headpiece in place against the prongs. The hair clip is opened by applying a manual force against the spring and retaining band.

11 Claims, 9 Drawing Sheets

HAIR CLIP RETENTION SYSTEM FOR HEADPIECE OF COCHLEAR IMPLANT SYSTEM

This application claims the benefit of U.S. Provisional Application Ser. No. 60/097,965, filed Aug. 26, 1998; and U.S. Provisional Application Ser. No. 60/087,654, filed Jun. 2, 1998.

BACKGROUND OF THE INVENTION

Cochlear implant systems are used to provide the sensation of hearing to those who are profoundly deaf, and for whom traditional hearing aids are of little or no assistance due to disease or damage to the middle ear or inner ear. A cochlear implant system provides the sensation of hearing by applying electrical stimuli to the inside of the scala tympani duct of the cochlea, thereby directly stimulating the ganglion cells coupled to the auditory nerve. Once stimulated, such ganglion cells send nerve impulses to the brain through the auditory nerve which are sensed in the brain as perceived sound.

A cochlear implant system typically includes implanted and external components. The implanted components include a pulse generator and an electrode, inserted into the cochlea, through which the electrical stimuli are applied. The external components include a power source, a microphone, a speech processor, and a headpiece. The microphone senses sound waves in conventional manner and converts such sensed sound waves to an electrical signal. This electrical signal is then processed by the speech processor and converted into an appropriate control signal for sending to the implanted pulse generator (also referred to as an "implanted stimulator"). A representative cochlear implant system is described in U.S. Pat. No. 5,776,172, incorporated herein by reference.

In operation, the control signal is sent to the implanted pulse generator through a transmission coil located in the headpiece, and is received through a corresponding coil included within the implanted pulse generator. In order to operate efficiently, i.e., in order for the headpiece to be able to transcutaneously send the control signal (i.e., transmit the control signal through the skin) to the implanted pulse generator, it is necessary that the external transmission coil of the headpiece be placed as close as possible to, and be properly aligned with, the receiving coil within the implanted pulse generator.

The most common technique for retaining the transmitting coil in a transcutanious-type cochlear implant system is the use of two magnets. One magnet is placed inside the implanted stimulator in the center of the receiving coil. The other magnet forms part of the transmitting coil.

The use of two magnets as described is very simple, effective and cosmetically attractive. However, there are a growing number of patients who are either unable or do not want to use this technique due to, inter alia, the concern that the internal magnet may interfere with MRI (magnetic resonance imaging) diagnosis.

To address such concerns, cochlear implant manufacturers have considered providing a number of options for holding the headpiece of the cochlear implant system in alignment with the implanted portion. Examples of such options include:

1. a non-magnetic implant;
2. an ear mold retention mechanism;
3. attachment of the headpiece to the arms of spectacles or eye glasses;
4. gluing the headpiece to the shaved skin with adhesive tape;
5. holding the headpiece in place with a headband; or
6. using other alignment/holding components and devices, glued to the skin, such as shown in U.S. Pat. No. 5,545,191, also incorporated herein by reference.

Disadvantageously, all of the above-listed alternatives have significant limitations. First, they are generally strongly dependant on the customization of the products to suit the individual anatomical requirements of the patients. In the case of ear mold retention, it is not cosmetically attractive, and for some patients, not a comfortable solution.

There is thus a need for a more universal, cosmetically acceptable, and more comfortable solution for holding the headpiece of a cochlear implant system in alignment with the receiving coil of an implanted stimulator.

SUMMARY OF THE INVENTION

The present invention addresses the above and other needs by providing a hair clip that holds the headpiece of a cochlear implant system in a desired location on the user's head. More particularly, the present invention provides a hair clip retention system that retains a transmitting coil in a transcutaneous-type cochlear implant.

Such system, in one embodiment, uses one magnet which forms part of the transmitting coil. A comb forms part of the retention system and has central teeth that are made from ferromagnetic material, and typically also has a non-central teeth that are made from non-ferromagnetic material. The comb is placed and secured in the patient's hair over the area where a cochlear implant is implanted. The transmitting coil is then placed next to the comb, and the magnet within the transmitting coil attaches to the ferromagnetic teeth of the comb.

In another embodiment, the transmitting coil is housed in a headpiece, and the headpiece and a comb are fastened together, along an edge of the comb where the teeth are bonded, with a hinge attachment spring.

In another embodiment, the headpiece is held by or otherwise attached to, a hair clip. The hair clip, in turn, is then clipped into the hair of the user at the desired location on the user's head.

Further embodiments are illustrated in the drawings.

It is thus an object of the present invention to provide a cosmetically attractive, comfortable, simple, inexpensive way to attach the headpiece of a transcutaneous-type cochlear implant system, which headpiece includes a transmitting coil, in alignment with an implanted receiver in a way that satisfies the anatomical requirements of a particular patient.

BRIEF DESCRIPTION OF THE DRAWINGS

The above and other objects, features and advantages of the present invention will be more apparent from the following more particular description thereof, presented in conjunction with the following drawings, wherein.

Corresponding components or elements in the various drawing figures are referenced with the same reference numeral.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The invention can be used by most patients providing they have some hair growth over the cochlear implant area to a minimum length of about 20 mm.

Figure 1A:
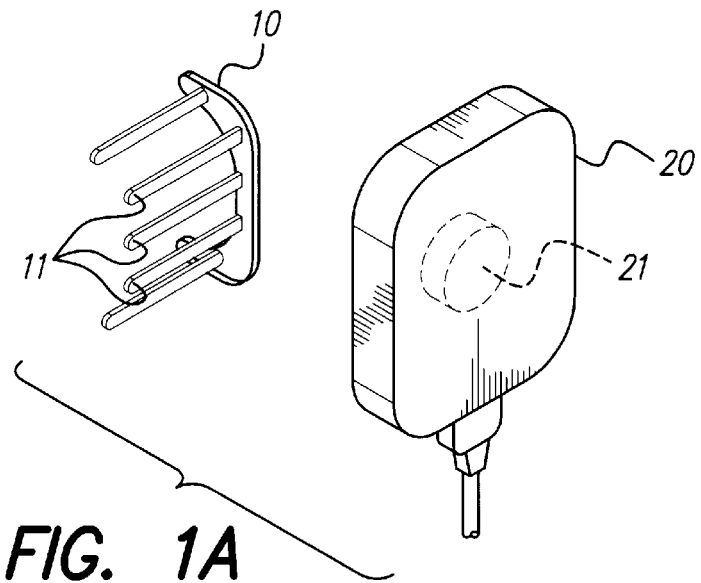
FIG. 1A shows a perspective view of a retention system made in accordance with the invention, such system including a comb having, in one embodiment, ferromagnetic teeth, and a headpiece, or transmitting coil, having a magnet therein.
Figure 1B:
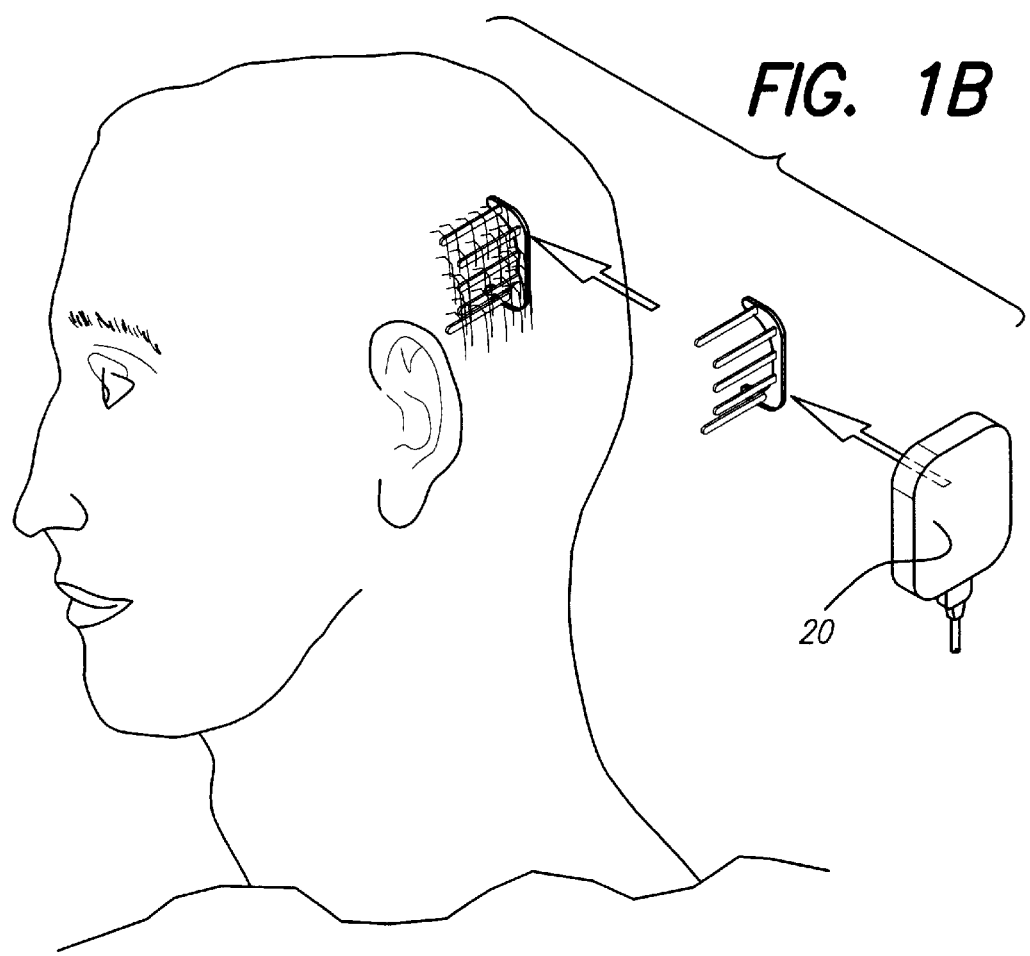
FIG. 1B illustrates the manner of attaching the comb to the hair of a patient, and then attaching the headpiece to the comb, thereby forming the hair clip of the invention.

In accordance with one embodiment of the invention, a retention system invention includes two major parts as shown in FIGS. 1A and 1B. The first part is a comb 10, with a number of teeth 11, made from ferromagnetic material, such as plated steel. To reduce transmission losses in the implant, only a few teeth, e.g., three teeth, in the center of the comb should be ferromagnetic. The other teeth, i.e., non-central teeth, may be made from a non-ferromagnetic material, such as plastic or aluminum.

Figure 2:
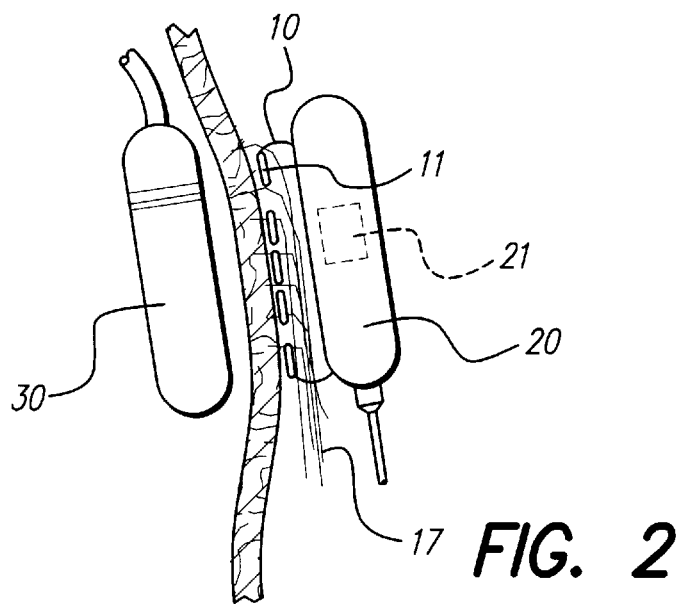
FIG. 2 shows a side schematic view illustrating the relationship between the implanted receiver and the comb and headpiece in accordance with the invention.

In use, the comb 10 is pushed in a horizontal direction into the hair, close to the scalp, directly over the cochlear implant area. A transmitting coil, typically housed in a headpiece assembly 20, is placed over the comb 10. A magnet 21 inside the headpiece 20 is attracted to the ferromagnetic central teeth 11 of the comb. As a result, the hair 17, threaded through the comb teeth, is trapped between the surface of the teeth 11 and the surface of the headpiece 20. The resulting pressure provides secure and close positioning of the headpiece 20 in reference to an implanted stimulator 30, as seen in FIG. 2.

Figure 3:
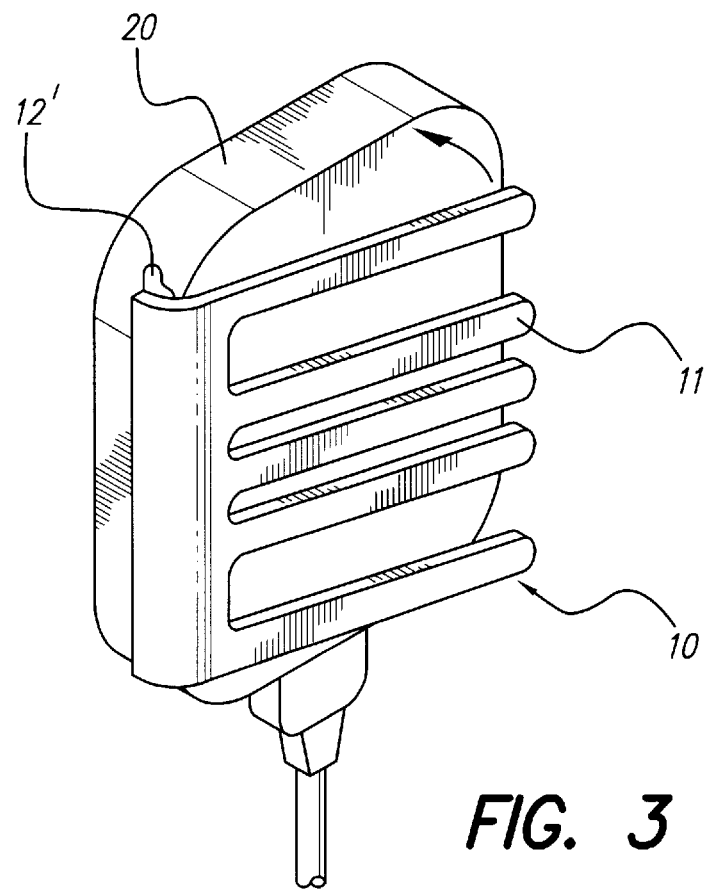
FIG. 3 depicts an alternative embodiment of the invention wherein the comb is attached by way of a hinge attachment at its edge where the teeth are joined to the headpiece. Such embodiment may further employ a separate spring which provides compression between the comb and the headpiece, thereby removing the requirement to employ a magnet inside the headpiece.

In an alternative embodiment, the comb 10 and coil 20 may be permanently joined together by a hinge attachment 12' along the same edge where the teeth are bonded, as seen in FIG. 3.

A similar principle of retention may be utilized by providing a separate spring as part of the hinge attachment, which provides compression between the comb 10 and headpiece 20. In such instance, the magnet 21 inside the headpiece may not be necessary.

Figure 3A:
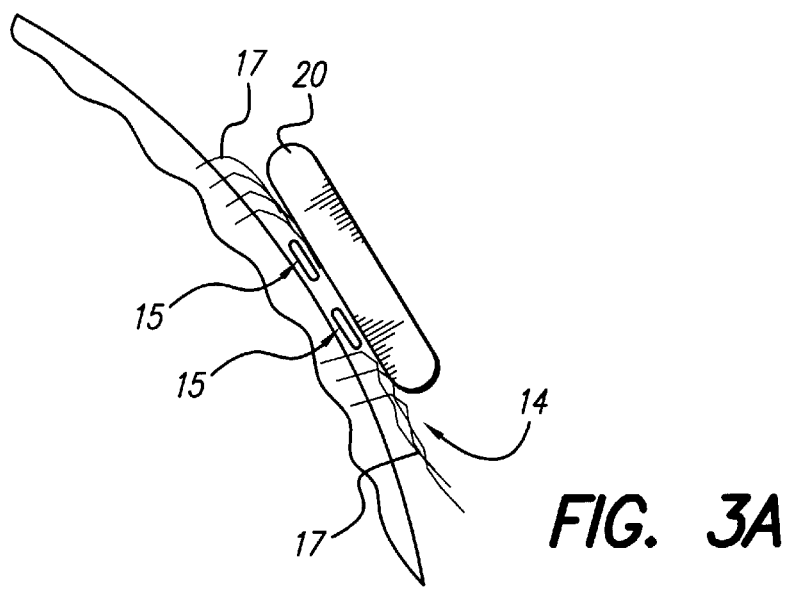
FIG. 3A shows a schematic side view of yet another embodiment of the invention wherein a two-prong retention hair clip holds the headpiece against the head of the user.

Another embodiment of the invention is realized using a hair clip 14, having prongs 15, e.g., two prongs 15, as shown in FIG. 3A. The prongs 15 are hinged to the body of the clip 14 to facilitate insertion of the prongs into strands 17 of the patient's hair. Different mechanisms may be used with the hair clip 14 in order to lock the headpiece 20 in place within the clip.

Figure 4A:
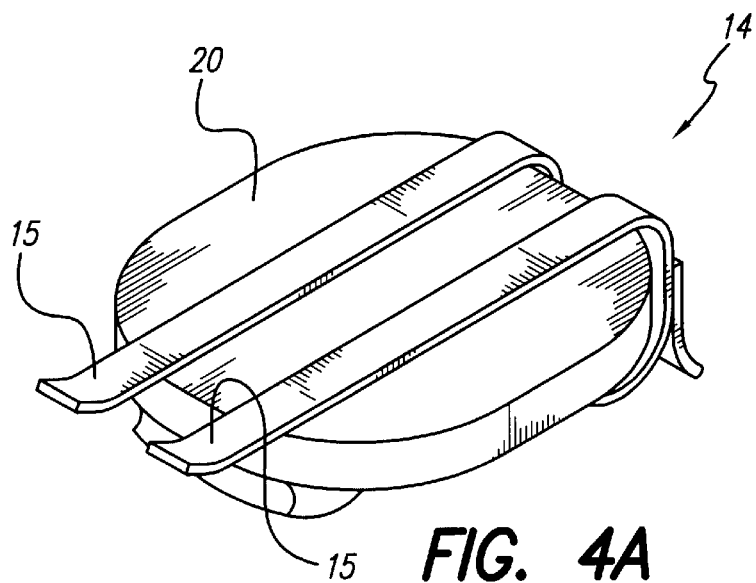
FIGS. 4A, 4B and 4C provide various views of the retention clip of FIG. 3A wherein a flat spring locking mechanism is utilized to hold the headpiece within the retention clip.
Figure 4B:
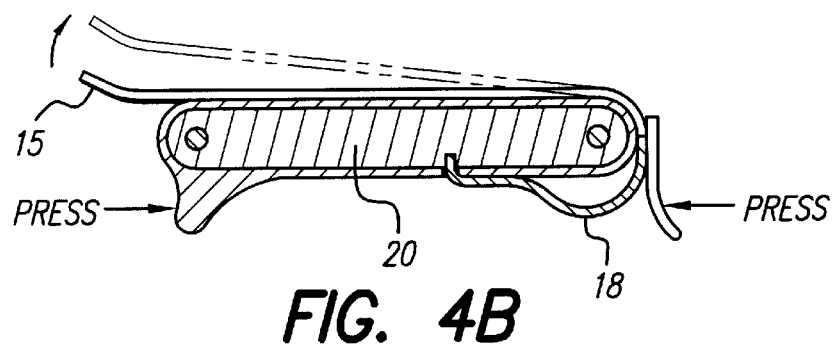
Figure 4C:
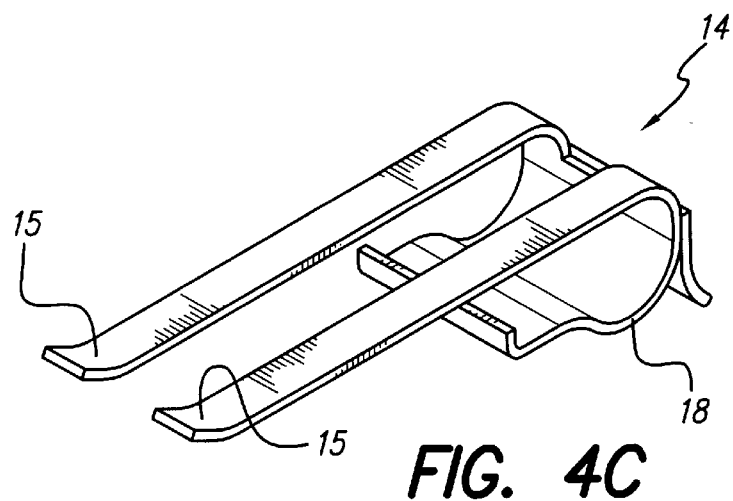

For example, as shown in FIGS. 4A, 4B and 4C, a flat spring 18 may be used to lock the headpiece 20 within the hair clip. FIG. 4A shows a perspective view of the retention hair clip 14 with a headpiece 20 secured therein. FIG. 4B shows a side view of the retention hair clip 14, and illustrates how application of pressing forces opens the prongs 15 and allows the headpiece 20 to be removed. FIG. 4C illustrates the retention clip 14 with the headpiece removed. The spring member 18, as well as the prongs 15, provide a compression force which securely holds the headpiece within the clip.

Figure 5A:
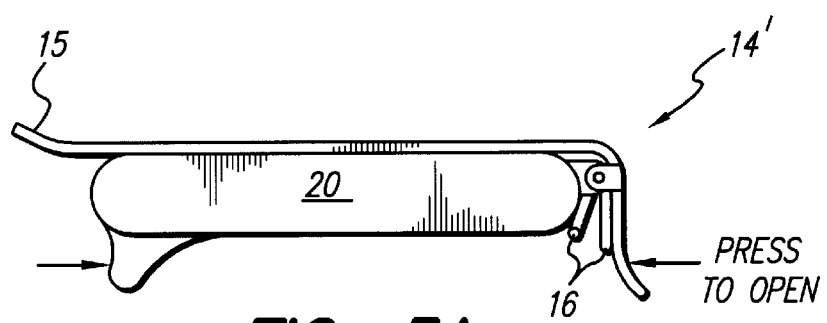
FIG. 5A shows a variation of the retention clip of FIG. 3A wherein a coiled spring is used as the locking mechanism for holding the headpiece within the retention clip.
Figure 5B:
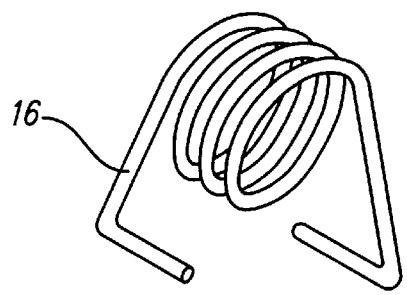
FIG. 5B shows the coiled spring used within the retention clip of FIG. 5A.

FIG. 5A shows an alternative embodiment of a retention hair clip 14' wherein a coil spring 16 provides the compressive locking force that holds the headpiece 20 within the clip. FIG. 5B is a perspective view of the locking coil spring 16.

Figure 6A:
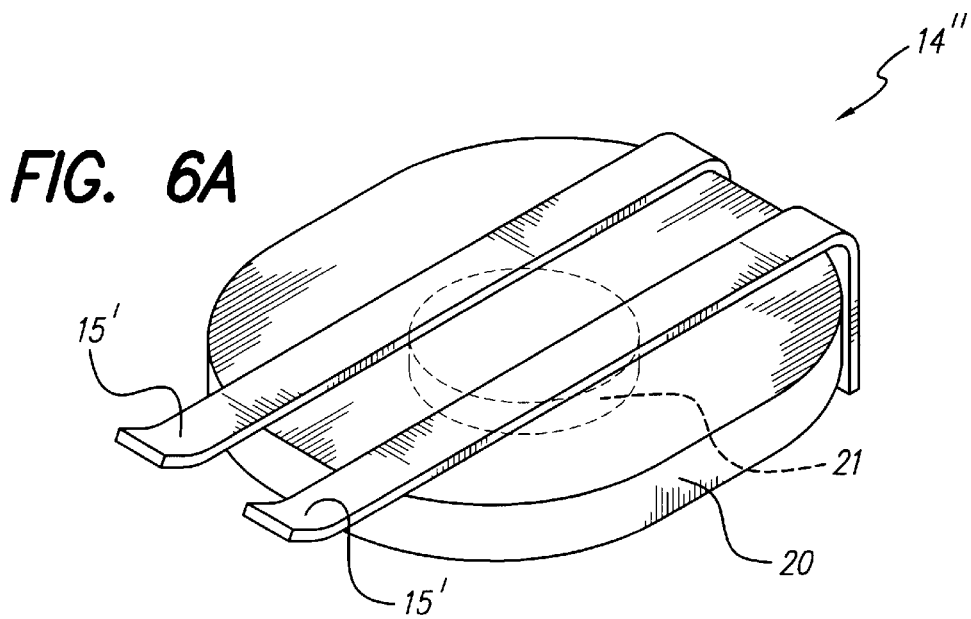
FIGS. 6A, 6B and 6C show another variation of the retention clip of FIG. 3A wherein a magnetic force is used to hold the headpiece within the retention clip.
Figure 6B:
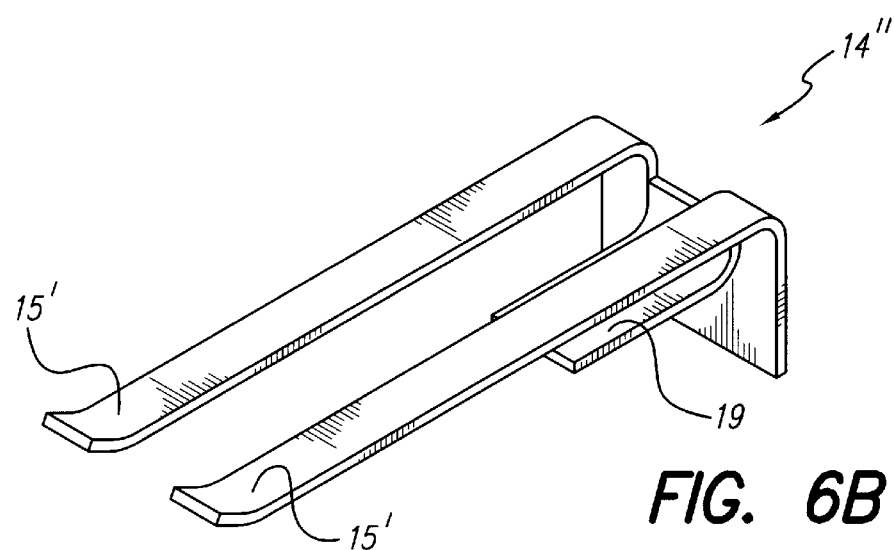
Figure 6C:
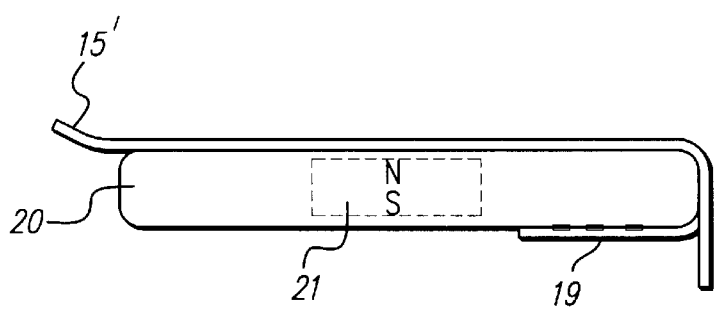

FIGS. 6A, 6B and 6C illustrate yet another variation of the hair clip 14" wherein a magnetic force is utilized to lock the headpiece in position within the clip. For the embodiment shown in FIGS. 6A, 6B and 6C, the prongs 15' of the clip are made from a suitable ferromagnetic material, e.g., steel, and may be coated with a suitable non-magnetic coating, such as a thin layer of plastic or latex, if desired. A magnet 21, included within the headpiece 20, is magnetically attracted to the magnetic prongs 15', and such attraction is sufficient to hold the headpiece 20 in its desired position against the prongs 15'. A flexible hinge 19, fixed to the body of the clip 14", may be included as part of the clip in order to facilitate opening the prongs of the clip so that the prongs 15' may be inserted into the strands of hair of the wearer.

As described above, it is thus seen that the retention system provided by the invention advantageously traps hair between the comb's teeth or clip's prongs and the headpiece, thereby firmly holding the system in a desired position above the implant location.

It is further seen that utilization of the headpiece magnet may provide a compression force between the comb's teeth or clip's prongs and the headpiece surface.

Figure 7:
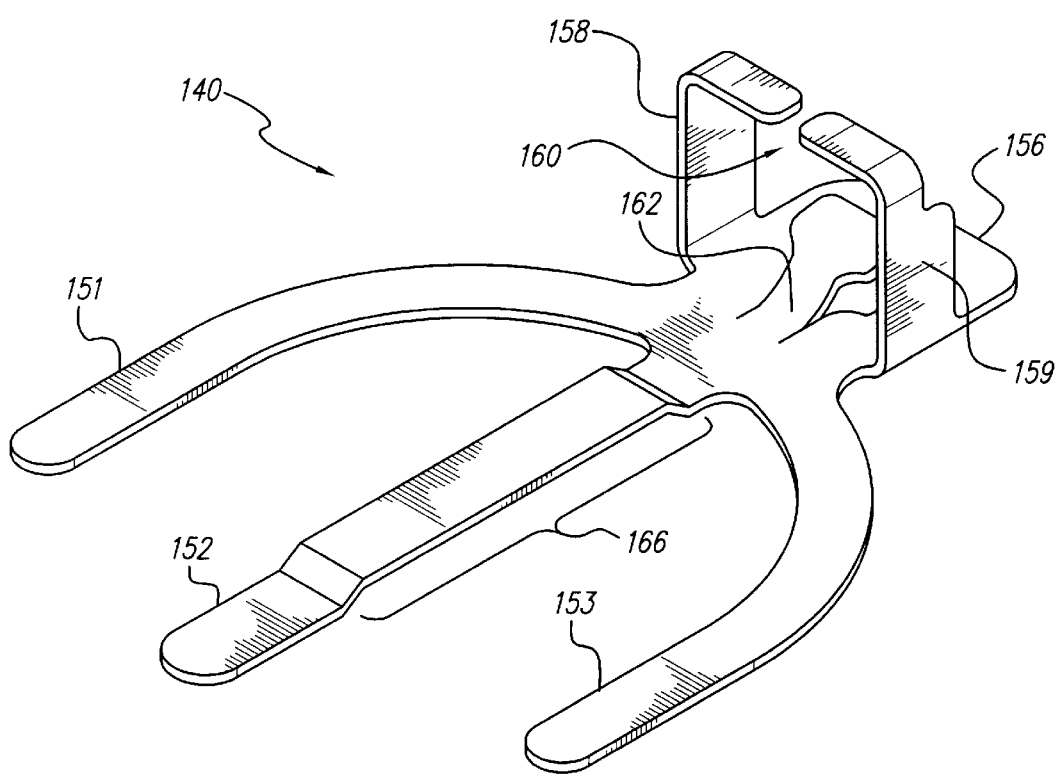
FIG. 7 is a perspective view of still another embodiment of the invention, which embodiment comprises a three-prong hair clip fashioned to hold the headpiece.

Turning next to FIGS. 7, a perspective view of still another embodiment of a hair clip 140 made in accordance with the present invention is illustrated. The embodiment shown in FIG. 7 offers of the advantage of being able to be easily made from a single sheet of material, e.g., stainless steel, through a straightforward stamping and forming (folding) operation. The embodiment illustrated in FIG. 7 shows a hair clip 140 having three prongs 151, 152 and 153.

Figure 7A:
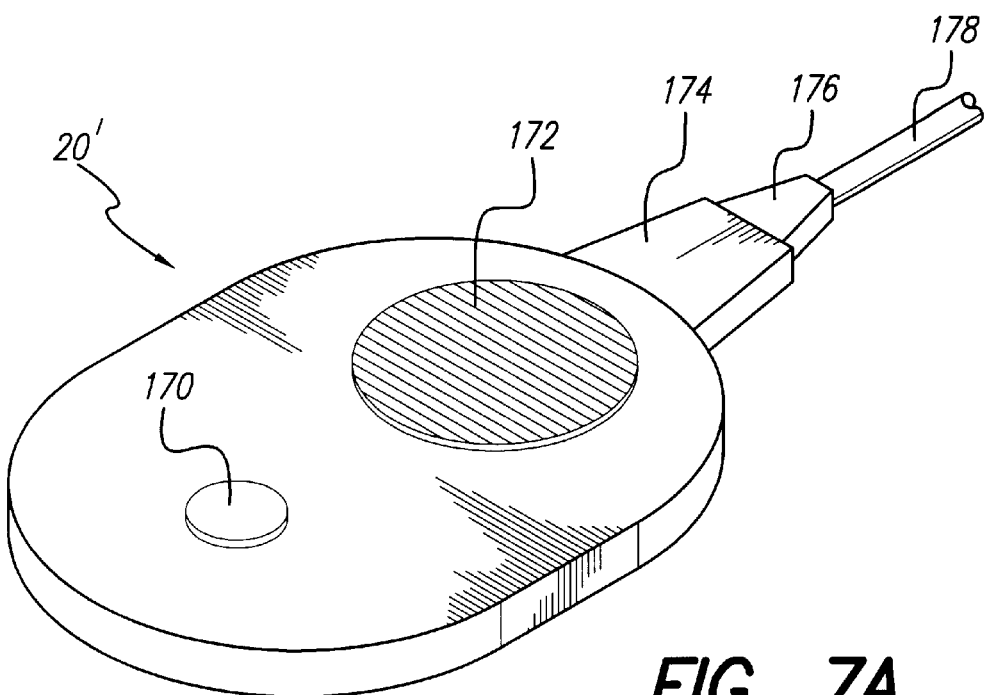
FIG. 7A is a generally top view of a headpiece of a cochlear implant system intended for use with the hair clip of FIG. 7.
Figure 7B:
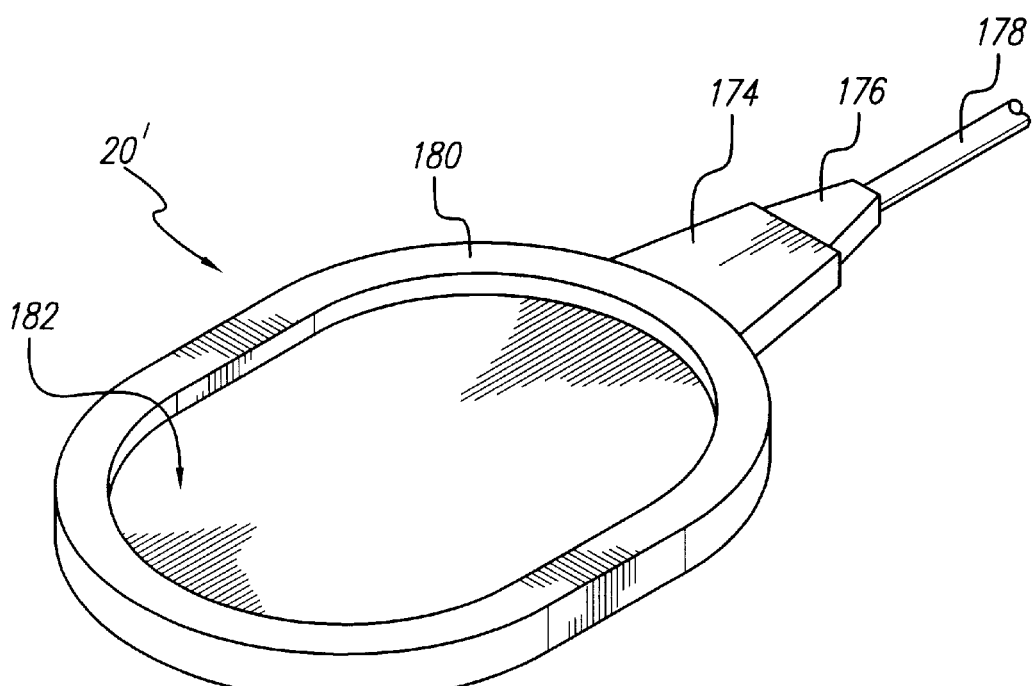
FIG. 7B is a bottom view of the headpiece used with the hair clip of FIG. 7.

The hair clip 140 shown in FIG. 7 is intended to be used with a head piece assembly 20' of the type shown in FIGS. 7A and 7B. FIG. 7A illustrates the top view of a preferred head piece assembly 20', and FIG. 7B shows a bottom view thereof. The "top" of the headpiece assembly 20', shown in FIG. 7A, is that portion that, in use, faces away from the scalp of the user. As seen in FIG. 7A, the top side of the headpiece assembly 20' may include a microphone opening 170, through which acoustic sound waves may be sensed by a microphone housed inside of the headpiece assembly, as well as a pattern of ridges 172 that facilitates holding the headpiece assembly 20' with the fingers without slippage.

The "bottom" of the headpiece assembly 20', shown in FIG. 7B, typically includes a ridge 180 around the perimeter of the assembly, which ridge 180 defines a shallow indentation 182 within the central portion of the bottom edge of the headpiece. Such indentation facilitates placement of the headpiece assembly 20' against a slightly curved surface, such as the scalp of the user.

As seen in both FIG. 7A and FIG. 7B, the headpiece assembly 20' further includes a pigtail portion 174 that protrudes from one side thereof. It is through this pigtail portion 174 that a cable 178, carrying the wires that connect the electrical components, e.g., microphone and transmitting coil, housed within the headpiece assembly 20' with an external speech processor and power source. This cable 178 may be further secured to the headpiece assembly 20' and pigtail portion 174 with a flexible restraining and reinforcing bracket 176 in order to further protect the cable 178 from being detached or pulled apart from the headpiece assembly.

The completed headpiece assembly 20', as shown in FIGS. 7A and 7B, is typically molded from a suitable polymer of an appropriate hardness, to form an integral assembly that cannot be opened or tampered with in any way by the user, and which is comfortable when worn adjacent the user's scalp for long periods of time.

Figures 8, 9B:
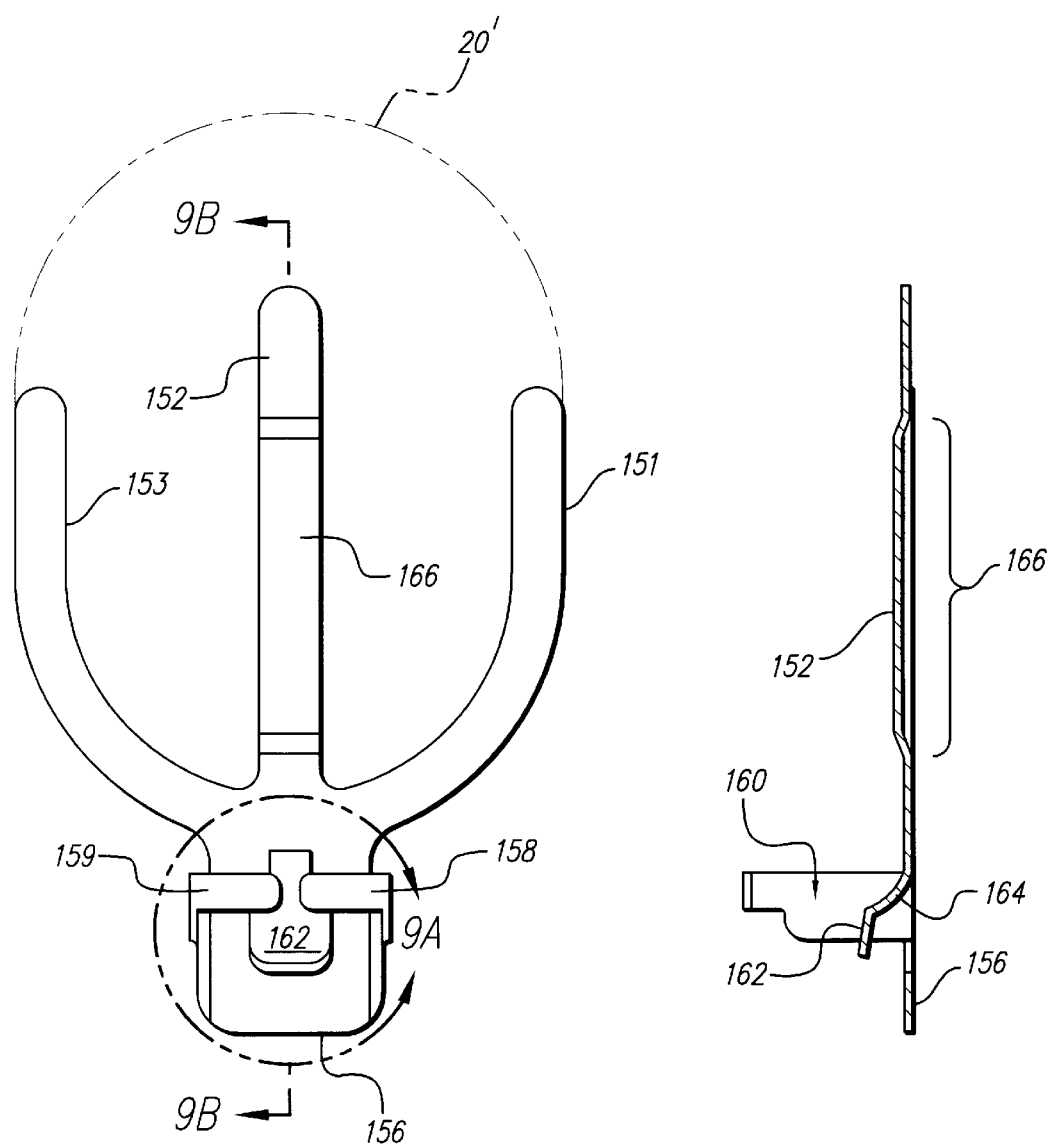
FIG. 8 shows a top view of the three-prong hair-clip of FIG. 7.
FIG. 9B is a sectional view of the hair clip of FIG. 8 taken along the lines 9B—9B of FIG. 8.
Figure 9A:
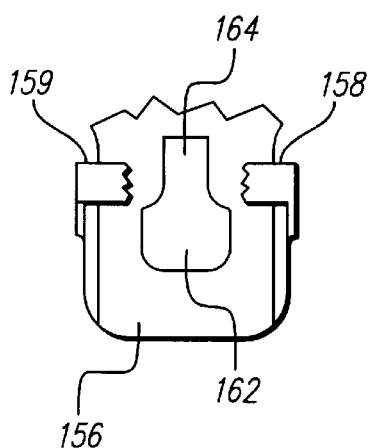
FIG. 9A is a detail view of the base portion of the hair clip of FIG. 8 (the portion in FIG. 8 encircled by the arrow 9A)
Figure 9D:
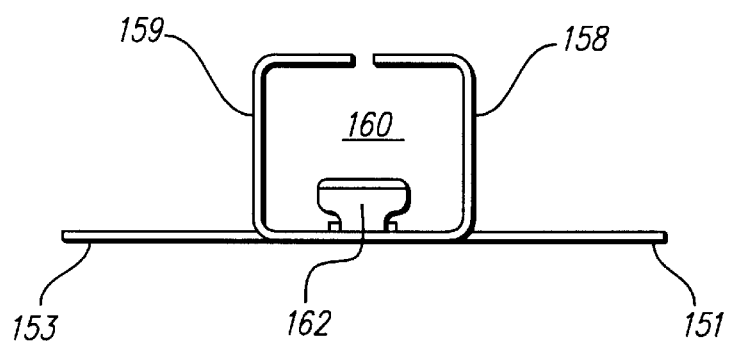
FIG. 9D shows an end view of the hair clip of FIGS. 7 and 8.
Figure 9C:
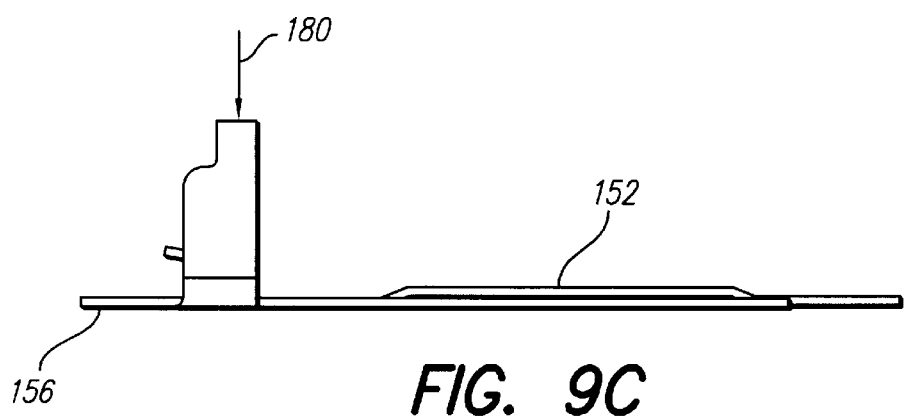
FIG. 9C shows a side view of the hair clip of FIGS. 7 and 8.

The three-prong hair-clip 140 of FIG. 7 is further illustrated in FIG. 8, which shows a top (or plan) view of the hair clip 140; FIG. 9A, which shows a detail view of the base section or portion of the hair clip 140 (i.e., the portion in FIG. 8 encircled by the arrow 9A); FIG. 9B, which shows a sectional view of the hair clip 140 taken along the lines 9B—9B of FIG. 8; FIG. 9C, which shows a side view of the hair clip 140; and FIG. 9D, which shows an end view of the hair clip 140.

As seen in these figures, the three prongs 151, 152 and 153 are joined at a base section 156. The base section 156 further includes side arms 158 and 159 that are bent up and folded to define a rectangular-shaped receiving band 160.

Centrally located, more or less, in the base section 156, as seen best in FIG. 9A, is a tab 162. The tab 162 comprises one end of a stem 164, which stem 164 is integrally connected to the base section 156. As seen in the drawings, the stem 164 may be narrower than the tab 162. The stem 164 bends up from the base portion 156 in a curved manner as seen best in FIG. 9B. The tab 162 is then bent at an angle (relative to the plane of the base portion) that is approximately 9 degrees, as also seen in FIG. 9B.

In use, the pigtail portion 174 of the headpiece assembly 20' is inserted through and into the receiving band 160 of the hair clip 140. As the pigtail portion 174 is inserted into the receiving band 160, the bent up tab 162, with its bent-up stem 164, securely holds the headpiece assembly 20' within the hair clip; and further functions as a spring that holds the prongs 151, 152 and 153, securely against the bottom edge of a headpiece assembly 20'.

The center prong 152 includes a portion 166 that is offset or indented so as to reside above the plane of the prongs 151 and 153 about 0.02 inches, or other suitable amount, so as to reside within the shallow indentation 182 formed within the base of the headpiece assembly 20'.

When installed or mounted on the hair clip 140, the headpiece assembly 20' engages the prongs 151, 152 and 153, substantially as shown in FIG. 8, wherein the outline of the edge of the headpiece assembly 20' opposite the pigtail portion 174 is shown by a dashed line. When thus mounted, the side prongs 151 and 153 engage the ridge 180 of the headpiece assembly 20', and the offset portion 166 of the center prong 152 engages the bottom of the shallow indentation 182.

To open the hair clip 140, after the headpiece assembly 20' has been mounted thereon, the user simply applies a pressing force between the lower portion of the base 156 and an upper edge of the pigtail portion 174, as shown in FIG. 9C. Such pressing force causes the prongs 151, 152 and 153 to pivot about a pivot point 180, defined by the upper edge of the arms 158 and 159 at the point where they engage an upper edge of the pigtail portion 174, thereby causing the prongs to "open" and provide a space between the prongs and the lower surface of the headpiece assembly into which the user's hair may be placed. Removal of such pressing force causes the three prongs to be firmly pushed against the lower surface of the headpiece assembly by the spring action created by the tab 162 and stem 164, which are bent up from the base portion 156, thereby firmly holding the hair clip to the user's hair which is gripped between the lower surface of the headpiece assembly and the prongs.

The hair clip 140 may be made by stamping a pattern of the clip from a single sheet of a suitable material. A preferred material is stainless steel, e.g., 17-7PH stainless steel, having a thickness of 0.016 inches. Once the pattern is stamped, any sharp edges that remain may be removed by tumbling or other means. After the sharp edges are removed, the arms 158 and 159 are bent and folded, as shown in the drawings, in order to define the rectangular-shaped receiving band 160 into which the pigtail portion 174 of the headpiece assembly 20' is to be inserted. After forming, the stainless steel may be heat treated to full hardness, as is known in the art.

The size of the hair clip 140 is determined by the size of the headpiece assembly 20' it is intended to carry. The dimensions described below are expressed in inches, and are intended to illustrate a preferred size of the hair clip 140 for use with a preferred headpiece 20. Such dimensions are not intended to be limiting, but are merely exemplary of representative dimensions that may be used. Representative dimensions for the hair clip 140 include an overall length (from the far edge of base portion to the distal tip of the center prong 152) of about 1.5 inches, e.g., 1.47 inches, and from the edge of the base portion to the distal tip of the side prongs 151 and 153 of about 1.3 inches, e.g., 1.27 inches. The width of the hair clip 140, as measured from the outside edges of side prongs 151 and 153, is about 1 inch, e.g., 1.06 inches. The height of the rectangular-shaped receiving band 160 is about 0.333 inches, and the width thereof is about the same, preferably tapering from a width near the base portion of about 0.315 inches to a width near the top of about 0.394 inches.

For some applications, the prongs 151, 152 and 153, and/or the entire exposed surface of the hair clip 140, may be coated with latex to provide a better surface for gripping hair.

As described above, it is thus seen that utilization of a spring, e.g., as part of a hinge attachment between the headpiece and comb or clip, as shown in FIGS. 4, 5 and 6, or as an integral part of a single-piece hair clip, as shown in FIGS. 7, 8 and 9, compresses the comb's teeth or clip's prongs against the headpiece assembly, thereby eliminating the need for a magnet in the headpiece.

It is further seen that the invention provides a cosmetically attractive, comfortable, simple, inexpensive way to attach a headpiece assembly, containing a transmitting coil of a transcutaneous-type transmission system, to an implanted receiver in a way that satisfies the anatomical requirements of a particular patient.

While the invention herein disclosed has been described by means of specific embodiments and applications thereof, numerous modifications and variations could be made thereto by those skilled in the art without departing from the scope of the invention set forth in the claims.

What is claimed is:

1. Apparatus for holding an external transmitting coil against the skin of a patient in an aligned position proximate an implanted receiving coil, comprising:
    a comb, with a plurality of central teeth, made from ferromagnetic material, and with a number of other teeth made from a non-ferromagnetic material;
    a headpiece assembly having an external transmitting coil and a magnet therein;
    whereby hair of the patient may be trapped between the teeth of the comb in order to position and hold the comb in a desired position relative to the implanted receiving coil, and
    wherein the magnet in the transmitting coil attaches to the ferromagnetic central teeth of the comb, thereby holding the headpiece assembly in a desired position relative to the comb.

2. The apparatus of claim 1 further including a hinge attachment for joining the headpiece assembly and the comb along an edge of the comb where the teeth are bonded.

3. The apparatus of claim 2 wherein the hinge attachment holds the headpiece assembly and comb together with a compression force.

4. Apparatus for holding an external transmitting coil against the skin of a patient in an aligned position proximate an implanted receiving coil, comprising:
    a comb having a plurality of teeth;
    a headpiece assembly having an external transmitting coil; and
    a spring attached to the headpiece and to the comb along an edge of the comb where the teeth are bonded that provides compression between the comb and headpiece assembly.

5. A comb, comprising:
    a plurality of central teeth, the central teeth being made from a ferromagnetic material, and
    a plurality of non-central teeth, the non-central teeth being made from a non-ferromagnetic material;
    whereby a magnet may be attached to the central teeth and held in position against such ferromagnetic teeth.

6. A clip, comprising:
    a plurality of prongs made from a ferromagnetic material, and
    a flexible hinge fixed to the clip for receiving a headpiece, whereby a magnet within the headpiece may be detachably held in position against the ferromagnetic prongs.

7. Apparatus for holding an external transmitting coil against the skin of a patient in an aligned position proximate an implanted receiving coil, comprising:
    a hair clip having a plurality of prongs;
    a headpiece assembly having an external transmitting coil; and
    a spring attached to the headpiece and to the clip that provides compression between the clip and headpiece assembly.

8. A headpiece hair clip for holding a headpiece assembly of a cochlear implant system against the skin of a user in an aligned position proximate an implanted stimulator, the headpiece assembly comprising a circular or oval shaped housing defining a volume wherein electrical and other components of the cochlear implant system may be housed, the headpiece assembly having a pigtail portion extending from one edge thereof, the hair clip comprising:
    a plurality of prongs extending from and integrally joined with a base portion;
    first and second side arms extending from and integrally joined with the base portion, wherein the first and second arms are folded upwardly and inwardly from the base portion to define a receiving band, wherein when the headpiece assembly is mounted on the hair clip the pigtail of the headpiece assembly may be inserted into the receiving band while a bottom surface of the headpiece assembly is positioned against an upper edge of the plurality of prongs;
    a tab cut from the base portion and bent upwardly to extend generally towards the receiving band;
    wherein the bent tab engages the pigtail of the headpiece assembly when the headpiece assembly is mounted on the hair clip, and wherein the bent tab functions as a spring that holds the plurality of prongs against the bottom surface of the headpiece assembly, and further wherein a pressing force applied between the base portion and an upper edge of the receiving band opens the hair clip by moving the plurality of prongs away from the bottom surface of the headpiece assembly.

9. The headpiece hair clip of claim 8 wherein the number of prongs comprises three, a center prong that engages the bottom surface of the headpiece assembly generally in the middle thereof, and two side prongs, each of which engages opposing edges of the bottom surface of the headpiece assembly, when the headpiece assembly is mounted on the hair clip.

10. The headpiece hair clip of claim 9 wherein the bottom surface of the headpiece assembly has a ridge around its periphery, thereby defining a cavity surrounded by the ridge, and further wherein the center prong of the hair clip includes an offset portion, the offset portion being adapted to engage a bottom surface of the cavity of the headpiece assembly at the same time that the two side prongs engage the ridge around the periphery of the bottom surface of the headpiece assembly.

11. The headpiece hair clip of claim 9 wherein the hair clip, including its three prongs, tab, first and second side arms, and base portion, is made from a single sheet of stainless steel that has been stamped into a hair clip pattern, and wherein the first and second side arms and tab are bent and folded upwardly from a plane defined by the single sheet of stainless steel.

* * * * *